(12) United States Patent
Whang

(10) Patent No.: US 8,703,210 B1
(45) Date of Patent: Apr. 22, 2014

(54) ADDING CALCIUM AND BICARBONATE TO HUMAN BLOOD

(75) Inventor: Sang Y. Whang, Miami, FL (US)

(73) Assignee: Sang Lads, Inc., Miami, FL (US)

( * ) Notice: Subject to any disclaimer, the term of this patent is extended or adjusted under 35 U.S.C. 154(b) by 1330 days.

(21) Appl. No.: 11/200,569

(22) Filed: Aug. 10, 2005

(51) Int. Cl.
*A61K 33/10* (2006.01)
*A01N 59/06* (2006.01)

(52) U.S. Cl.
USPC ........... 424/687; 424/464; 424/468; 424/747; 427/2.21

(58) Field of Classification Search
USPC .................. 514/570; 424/464, 468, 687, 747; 427/2.21
See application file for complete search history.

(56) References Cited

U.S. PATENT DOCUMENTS 6,608,111 B1 * 8/2003 Meyers et al. ................ 514/570

FOREIGN PATENT DOCUMENTS

WO    WO - 98/21983    *  5/1998

OTHER PUBLICATIONS

Ittel et al., "Calcium Carbonate as a Phosphate Binder in Dialysis Patients: Evaluation of an Enteric-Coated Preparation and Effect of Additional Aluminum Hydroxide on Hyperaluminaemia", Jan. 1991, Journal of Molecular Medicine, vol. 69 No. 2, pp. 59-67.*

* cited by examiner

Primary Examiner — Ali Soroush

(57) ABSTRACT

A human consumable chemical compound of calcium carbonate which is coated with an impervious coating that will not allow the compound to dissolve from stomach acid but does allow it to dissolve in the aqueous environment of the intestine. The chemical compound is time released, and is positionally sensitive to reach the intestines of the human body where it is absorbed into the blood. Carbonic acid in the blood reacts upon the gradual dissolution of the compound and this reaction converts the calcium carbonate to calcium bicarbonate. Calcium bicarbonate in the blood neutralizes the body's harmful acidic wastes and is a substitute for drinking about fifty ounces of alkaline drinking water daily.

6 Claims, 1 Drawing Sheet

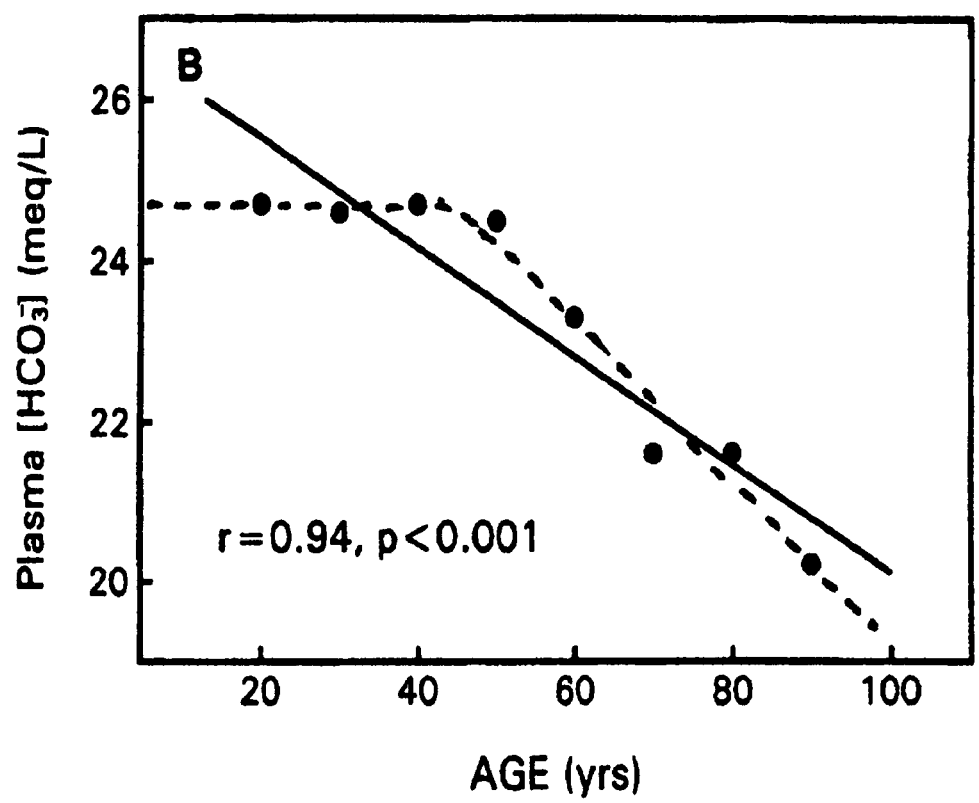

ADDING CALCIUM AND BICARBONATE TO HUMAN BLOOD

FIELD OF THE INVENTION

The field of the present invention relates broadly to methods and compounds pertaining to health. More specifically, the invention relates to a human consumable dry chemical compound of calcium carbonate, say in pill form, which carbonate reacts with carbonic acid in our blood. The result of this reaction is a conversion into calcium bicarbonate, thus supplying calcium bicarbonate into the blood.

Coating such a pill, tablet or the like with an enteric layer that sufficiently resists the effect of stomach acid, will assure the user that the pill compound will pass through the stomach. It then dissolves in the intestines for direct absorption into the bloodstream as calcium carbonate and changes into calcium bicarbonate in the bloodstream.

DESCRIPTION OF PRIOR ART

Diets and exercise are strongly recommended for today's life style. No diet or exercise, however, can effectively replenish bicarbonates to the blood. It is a known fact that we lose bicarbonates in our blood as we age. See, the Journal of Gerontology: BIOLOGICAL SCIENCES, 1996. Vol. 51A. No. 1, B91-B99, *Age and Systemic Acid-Base Equilibrium: Analysis of Published Data*, by Drs. Lynda Frassetto and Anthony Sebastian of the University of California, San Francisco, Department of Medicine and General Clinical Research Center.

From the dotted line of FIG. 1, we can see that a noticeable bicarbonate decline begins at the age of 45, and by the age of 90, we lose 18% of the bicarbonates ($HCO_3-$). Bicarbonates are the alkaline buffers that neutralize acid, resulting in the elimination of acidic wastes in our body. Decline of bicarbonates in the blood signal the beginning of acid-induced adult degenerative diseases. The age of 45 is the average age when symptoms of diabetes, hypertension, osteoporosis, etc. start to appear. The world totally missed the fact that the very cause of aging is the diminishing of bicarbonates in the blood.

I am the first to discover this fact and herein teach that replenishing bicarbonates in the blood is the way to prevent aging and also to prevent the age-related/acid-induced adult degenerative diseases. Even the author of the reference paper above, thinks the reduction of bicarbonates in the blood is an inevitable fact of life as we age. Dr. Frassetto's paper concludes that, as doctors treat kidney patients, they must treat old people differently from young people because old people have less bicarbonate in their blood.

Bicarbonates are found in human blood mainly in the form of potassium bicarbonate, sodium bicarbonate and calcium bicarbonate. A small amount of magnesium bicarbonates are present as well. As we age we lose bone density (osteoporosis) because the lack of alkaline minerals in the blood forces the body to rob calcium from our bones. Therefore, ideally, calcium bicarbonates are the best bicarbonates to supply to the blood.

We are told, therefore, to take calcium tablets as we age. However, calcium carbonate provided by calcium tablets, does not dissolve easily. Moreover, the calcium carbonate that does dissolve is destroyed by our stomach acid and becomes calcium salt and water and carbon dioxide.

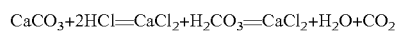

$$CaCO_3 + 2HCl = CaCl_2 + H_2CO_3 = CaCl_2 + H_2O + CO_2$$

Calcium bicarbonate is not available on the market. Apparently nobody can produce it. Perhaps the chemical compound is not stable enough to maintain in powder form. Indeed, it may require absolute zero humidity, which is very difficult to maintain. If calcium bicarbonates were available, the same techniques disclosed in my pending patent application, PCT/US04/18780 would have been applied.

Under such circumstances, the question may be posed: How does one go about getting calcium bicarbonate into our bodies? If presented in pill form, the calcium carbonate in the stomach will be destroyed by the stomach hydrochloric acid. Thus, the calcium carbonate never reaches the bloodstream.

Bicarbonates are relatively neutral and are considered by the medical community, to be neutral enough to be put directly into the blood stream. For example, at hospitals, it is known for revival purposes to inject sodium bicarbonate directly into the veins of patients coming to the emergency room in a comma caused by a low blood pH. But, that is different than my present invention. I don't teach injecting an alkaline solution to elevate the blood pH. Rather, this invention introduces calcium carbonate, an alkaline compound, into the bloodstream by enteric coating a calcium carbonate tablet and allowing the bodies natural processes to supply the much needed calcium bicarbonate to the blood.

DISCUSSION OF MY EARLIER PATENTS

The benefits, for example, of alkaline water are well set forth in my issued U.S. Pat. No. 5,306,511 ('511) and need not be repeated here. My United States ('130) patent discloses and claims dry oral units of a potassium bicarbonate and sodium bicarbonate in a time-released mixture.

It is accepted and understood that the accumulation of acid within and throughout the body contributes to the aging process and is a major cause of many adult degenerative diseases. There are many antacids on the market; however those are for the reduction of over-acidification of the stomach. These commercial antacids are for a different purpose and are of a different chemical compound.

Many drugs are wasting chemicals because they are not enteric coated and much of the drug is being lost in the stomach. Indeed, only a small portion of a given drug goes into the blood; thus pumping an unnecessary amount of chemicals into the body, which drugs often cause bad side-effects.

The pill of my '130 patent, uses what may be considered an insignificant amount of potassium and sodium. But, the pill, in time release form, is combined with an enteric coating in my pending patent application, PCT/US04/18780 and these minerals do much more than big doses of medicine which have adverse side-effects. Most of the enteric coatings in the past were used to protect the stomach walls from the damaging effects of drugs dissolving in the stomach.

Briefly stated, alkaline drinking water of increased oxygen having a pH in the range of about 8.5 to about 10.5 is created from ordinary tap water treated in accordance with my patented '511 invention. AlkaLife® of my '511 patent is an additive that assures a readily available source of alkaline water. Such water is made by simply adding a couple of drops of my patented additive to a 10 ounce glass of water in order to make the pH of the water about 10. It is recommended that five glasses of water, or about 50 ounces, should be consumed daily. Five glasses daily of alkaline water via my AlkaLife® additive enhances health and well being.

AlkaLife® of my '511 patent, reduces acidic waste by responding to the natural functioning of the human body. Thus, alkalinity of the water we drink is neutralized by the stomach acid, but the presence of my patented product raises the stomach pH higher. Our body, while trying to maintain the stomach pH in its original acid state, causes the stomach to produce more hydrochloric acid so that it may be injected into the stomach. In the process, our bodies develop bicarbonates which enter our blood and stand by as an alkaline buffer to destroy acidic wastes in our body, when needed.

$$H_2O+CO_2+NaCl=HCl+NaHCO_3$$

If there is no immediate acidic waste, the bicarbonates wait there as a blood buffer until acidic wastes do appear. Removing such harmful waste is critical for our continued health and longevity.

My '130 patent discloses and claims oral intake units of a potassium bicarbonate and sodium bicarbonate mixture which enters the human body in dry bicarbonate form. In my '130 patent a time release material is also associated with the pill, tablet, caplet or capsule. My research has shown, however, that added health benefits are achieved if the time-released compound of my '130 patent delivers its beneficial treatment capability directly into the intestinal tract. Disintegration in the stomach wastes the bicarbonates and thus diminishes the amount of beneficial results one may expect.

While my earlier patents have centered on bicarbonates of sodium and potassium, this present invention centers on calcium. Calcium bicarbonate is not available for formulation of a pill, and thus I have invented a calcium carbonate time release pill that is enteric coated to avoid damage by hydrochloric acid of the stomach. Once the pill has passed into the intestinal fluids, the pill dissolves and is absorbed into the blood stream. Carbonic acid in the blood converts the dissolved calcium carbonate into much needed calcium bicarbonate.

There are cases where a patient cannot take any potassium, as for example, a patient with kidney dialysis. For them calcium bicarbonate is a must. As we age we lose not only bicarbonates but also calcium. This is a well known fact. Most people over 60 suffer osteoporosis and they are told to take calcium pills. This new pill achieves two benefits with one stone: adding both bicarbonates and calcium to the blood.

SUMMARY OF THE PRESENT INVENTION

I claim using an alkaline mineral compound (a mineral compound dissolved in water that displays alkaline property) which is interjected directly into the bloodstream and takes advantage of carbonic acid ($H_2CO_3$) therein to neutralize it and thus provide bicarbonates to the blood. These alkaline mineral compounds must be enteric coated to avoid damage by the hydrochloric acid in the stomach. In particular, the mineral compound may take the form of calcium carbonate and my process yields calcium bicarbonate as a reaction with carbonic acid in the blood.

$$CaCO_3+H_2CO_3=Ca(HCO_3)_2=Ca^{++}+(HCO_3^-)_2$$

Magnesium may work in a similar manner (replace Ca with Mg in the above formula), but the amount of magnesium required by the human body, compared to calcium, is very small.

I respectfully submit that a positional-sensitive, time released disintegration of my alkaline mineral compound ("pill") is a significant discovery for creating highly necessary calcium bicarbonate in our blood stream. This discovery may very well foretell a major change for medicine of the future. Many of today's bad diseases that call for expensive medicines may disappear naturally if my teaching of this invention is widely accepted.

OBJECTS OF THE INVENTION

It is an object of this invention to neutralize and reduce the body's acidic waste products by a readily consumable chemical in pill form which is enteric coated so that the pill will not dissolve in the stomach but rather dissolves further along in the digestive process.

It is still a further object of this invention to provide, in an enteric coated pill form, a calcium compound that is converted into bicarbonate by reaction with carbonic acid naturally predominant in human blood.

It is still a further object of this invention to provide a pill-supplied source of calcium carbonate in an orally administered time release calcium pill having an outer coating of enteric material which dissolves only in the intestines so that the calcium carbonate pill combines with carbonic acid in the blood as calcium bicarbonate.

BRIEF DESCRIPTION OF THE DRAWING

FIG. 1, is taken from FIG. 2 of the Journal of Gerontology: BIOLOGICAL SCIENCES, 1996. Vol. 51A. No. 1, B91-B99, *Age and Systemic Acid-Base Equilibrium: Analysis of Published Data*, by Drs. Lynda Frassetto and Anthony Sebastian of the University of California, San Francisco, Department of Medicine and General Clinical Research Center. I have added the dotted line shown in my FIG. 1 to FIG. 2 of the Frassetto reference.

BACKGROUND OF THE INVENTION

I report herein the results of my experiment that confirms the basis of my discovery. Calcium carbonate powder dissolved into water may raise the pH as high as 9. When carbonic acid (in the form of club soda) is added to the mixture, the pH instantly drops to neutral. This is how I obtained the confidence that I can input calcium carbonate directly into the blood stream without worrying about elevating the blood pH too high.

Carbohydrates that we consume turn into carbonic acid. (Carbohydrate, completely burnt turns into carbon dioxide and water, thus becoming carbonic acid.) Our blood has so much carbonic acid that our lungs are constantly exhaling carbon dioxide, so as to not over acidify the blood. There is no shortage of carbonic acid in our blood, especially in our veins. The Columbia Encyclopedia states; "Calcium carbonate is largely insoluble in water but is quite soluble in water containing dissolved carbon dioxide, combining with it to form the bicarbonate." This invention, as explained below, takes advantage of this fact.

It is generally understood that more than 70% of our body is water and more than 90% of blood is water. With my time release and enteric coating features, the pill will be prevented from releasing all at once. Such a sudden release might increase too rapidly the amount of calcium bicarbonate that is created in the blood. Such a rapid release might, in some sensitive persons, result in a sensation of alkalosis. Time release guards against that possibility.

DESCRIPTION OF PREFERRED EMBODIMENT AND BEST MODE

Turning now to a detailed description of the invention, which may be understood without reference to any drawing, one must first briefly understand the human aging process. Aging is primarily marked by the accumulation of non-disposed acidic waste products that our cells produce as they burn nutrients to generate energy. We need to burn nutrients in order to function and live.

Acid coagulates blood and the accumulated acidic wastes of our bodies clog our capillary vessels and reduce blood circulation near the accumulated waste locations. It is postulated that this phenomena is the primary cause of adult diseases such as diabetes, kidney disease, and the like.

It is also believed important for an understanding of the invention, to note the effects of alkaline water in the human body. Drinking alkaline water neutralizes and reduces the acidic waste products created within our bodies. Thus, people drinking alkaline water have observed many health improvements over the years.

In accordance with this invention, alkaline water benefits are available in readily consumable chemical pill, tablet, capsule or caplet form. (These various forms are collectively referred to herein as a "pill".) Coating my '130 pill with an enteric coating, allows the dissolution to be positionally controlled at the exact location where such dissolution is most beneficial. Such a coating prevents the pill from dissolving prematurely in the stomach where benefits to be derived from the pill constituents are wasted. Thus, in my invention, the pill is dissolved in the intestine where its time release format can work the best. It is there in the intestine that the most beneficial results are achieved.

Additional inert compounds to make a pill a slow time release pill, or additional coating material that spreads out the pill's dissolution time are known in the art. In the relevant art a slow acting pill may be described by various terms such as extended release, sustained release, controlled release, delayed release, sustained action, continuous action and slow release. All of these terms mean essentially the same thing—namely, that the action of the pill is gradually spread out over an extended period of time.

I desire a time release period of about 5 to 7 hours inside the intestine. In about two hours, the pill, tablet, capsule or caplet will have cleared the stomach and will have entered into the user's intestines before any chemical dissolution may begin to take place. Enteric coating resists any disintegration while in the presence of the stomach acid environment. In the intestinal tract, however, the enteric coating dissolves away, and the favorable time release benefits of my invention become available.

To explain, please note that the blood in our bodies has ample amounts of dissolved carbon dioxide. That is where the calcium carbonate will be entering for reaction purposes. Even if the calcium carbonate was not fully dissolved, the calcium carbonate will become dissolved by reacting with the carbonic acid. Such a reaction produces ionization for the calcium compound.

When a chemical compound dissolves in water some part of the constituents split loosely and one side becomes charged as a positive polarity and the other side becomes charged to a negative polarity. For example, when a table salt NaCl dissolves in water, then it becomes Na+ and Cl—. In a similar manner $CaCO_3$, undissolved, remains neutral; however, dissolved in the presence of a carbon dioxide solution, it becomes $CA^{++}$ and $(HCO_3—)_2$.

As noted above, calcium has two positive charges and bicarbonate has one negative charge; therefore there must be two bicarbonates required in order to achieve an electrically equivalent match. Usually plus and minus signs are omitted by convention, but when we are denoting that it is dissolved in water and ionized, the + or − signs are shown in order to denote polarity, and also denote the fact that these molecules are ionized. In other words, the molecules are electrically active.

Water is $H_2O$ and obviously it is dissolved. However only one $H_2O$ molecule in 10,000,000 is ionized to be H+ and OH— in room temperature. In other words, the hydrogen ion concentration is one in 10 to the seventh power. We call this a pH of 7. There is a difference between dissolved and ionized. Some chemical compounds dissolve well but do not get ionized easily, while some chemical compounds dissolve and get ionized very easily. Alkaline minerals get ionized easily. Usually, the order of ionization ease is potassium, sodium, calcium and magnesium. Fortunately, calcium bicarbonate ionizes very easily.

What makes the calcium ionized? The answer is carbonic acid. In the absence of carbonic acid, calcium remains insoluble and non-ionized. Bicarbonate is very soluble in water and it caries a negative charge. Ionized means the particle is electronically charged either positive or negative. The ionization takes place in aqueous solution, in other words, in water. Without water, there is no alkalinity or acidity.

When a particle is charged it is active. It doesn't mean a free radical. There is a matching opposite polarity particle nearby but they are loosely bound. And if there is an oppositely charged particle which is stronger in attraction, it mates with it. Calcium carbonate does not dissolve easy in water. If it does not dissolve, it does not react with other substances. Even if it dissolves, if it is not ionized, it is not actively reacting with other chemicals.

Thus the calcium pill, after passing through the stomach, enters the "aqueous" intestinal area where it begins a time release dissolution. Then the capillary vessels in the intestinal walls suck the calcium carbonate molecules into the blood stream. As they enter the blood stream, the carbonic acid in the blood converts the calcium carbonate to calcium bicarbonate. Although we know that we lose calcium bicarbonates as we age, we now have an invention that assures a simple and secure replacement mechanism for those missing bicarbonates.

$$CaCO_3+H_2CO_3=Ca(HCO_3)_2=Ca^{++}+2(HCO_3^-)$$

While my invention has been described with reference to a particular example of preferred embodiments, it is my intention to cover all modifications and equivalents within the scope of the following appended claims. It is therefore requested that the following claims be given a liberal interpretation which is within the spirit and scope of my contribution to this art.

What is claimed is:

1. A single active ingredient tablet of calcium carbonate supplying calcium derived bicarbonate, said tablet consisting of:
   impurity free mineral calcium carbonate as the only active ingredient in said tablet;
   an enteric coating for said calcium carbonate tablet ensuring that the calcium carbonate will not be dissolved in the stomach but rather will be dissolved and absorbed inside the body's intestinal tract;
   wherein the calcium carbonate reacts with carbonic acid in the blood of the body's intestinal tract.

2. A method of changing calcium carbonate into calcium cation and bicarbonate—anion in vivo by oral administration of the tablet in claim 1.

3. The single active ingredient tablet in accordance with claim 1, further consisting of an intestinal time release ingredient in said tablet for controlling dissolving and absorbing of said calcium carbonate inside the body's intestinal tract.

4. A calcium carbonate tablet formulation supplying caclium carbonate derived bicarbonate when consumeed and consisting essentially of:
   a neutral, impurity free, blood soluble calcium carbonate powder,
   an enteric coating for said tablet, and having a sustained release absorption of said powder during travel in intestinal blood.

5. The calcium carbonate tablet in accordance with claim 4, wherein said sustained release is for a period of several hours.

6. The calcium carbonate tablet in accordance with claim 5, wherein said sustained release takes place in the intestinal blood of a consumer.

* * * * *